United States Patent
Bennet et al.

(10) Patent No.: US 12,089,960 B2
(45) Date of Patent: Sep. 17, 2024

(54) SENSOR TYPES AND SENSOR POSITIONING FOR A REMOTE PATIENT MONITORING SYSTEM

(71) Applicant: MAYO FOUNDATION FOR MEDICAL EDUCATION AND RESEARCH, Rochester, MN (US)

(72) Inventors: Kevin E. Bennet, Rochester, MN (US); Charles J. Bruce, Rochester, MN (US); Paul A. Friedman, Rochester, MN (US); Virend K. Somers, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 1920 days.

(21) Appl. No.: 16/311,116

(22) PCT Filed: Jul. 1, 2014

(86) PCT No.: PCT/US2014/045030
§ 371 (c)(1),
(2) Date: Dec. 18, 2018

(87) PCT Pub. No.: WO2015/002935
PCT Pub. Date: Jan. 8, 2015

(65) Prior Publication Data
US 2019/0223806 A1 Jul. 25, 2019

Related U.S. Application Data

(60) Provisional application No. 61/841,862, filed on Jul. 1, 2013.

(51) Int. Cl.
*A61B 5/0255* (2006.01)
*A61B 5/00* (2006.01)
(Continued)

(52) U.S. Cl.
CPC .............. *A61B 5/721* (2013.01); *A61B 5/053* (2013.01); *A61B 5/282* (2021.01); *A61B 5/366* (2021.01);
(Continued)

(58) Field of Classification Search
CPC .............. A61B 5/04085; A61B 5/0006; A61B 5/04087
See application file for complete search history.

(56) References Cited

U.S. PATENT DOCUMENTS

| 6,117,077 A | 9/2000 | Del Mar et al. |
| 8,229,537 B2 | 7/2012 | Chandrasekaran et al. |

(Continued)

FOREIGN PATENT DOCUMENTS

| CA | 2849294 A1 * | 3/2013 | ........... A61B 5/0464 |
| WO | WO-2007041946 A1 * | 4/2007 | ......... G06F 19/3406 |

OTHER PUBLICATIONS

International Search Report and Written Opinion for PCT/US2014/045030, mailed Dec. 31, 2014.
(Continued)

*Primary Examiner* — Michael J D'Abreu
(74) *Attorney, Agent, or Firm* — Faegre Drinker Biddle & Reath LLP

(57) ABSTRACT

This document provides devices and methods for monitoring health patient parameters using a wearable monitoring device. For example, this document provides monitoring devices with multiple sensors, multiple types of sensors, algorithms for managing the multiple sensors to enhance monitor performance, and for detection of health events using health parameter data that is acquired by the monitoring system.

19 Claims, 5 Drawing Sheets

(51) Int. Cl.
*A61B 5/053* (2021.01)
*A61B 5/282* (2021.01)
*A61B 5/366* (2021.01)
*A61B 5/0531* (2021.01)
*A61B 5/296* (2021.01)

(52) U.S. Cl.
CPC .......... *A61B 5/6823* (2013.01); *A61B 5/6833* (2013.01); *A61B 5/7207* (2013.01); *A61B 5/7246* (2013.01); *A61B 5/0531* (2013.01); *A61B 5/296* (2021.01); *A61B 2560/0412* (2013.01); *A61B 2560/0443* (2013.01); *A61B 2560/0462* (2013.01); *A61B 2560/0468* (2013.01); *A61B 2562/0219* (2013.01); *A61B 2562/164* (2013.01)

(56) References Cited

U.S. PATENT DOCUMENTS

| | | | |
|---|---|---|---|
| 2002/0077536 A1* | 6/2002 | Diab | A61B 5/14546 600/323 |
| 2008/0013747 A1* | 1/2008 | Tran | A61B 5/0295 381/67 |
| 2008/0033271 A1 | 2/2008 | Say et al. | |
| 2010/0081913 A1 | 4/2010 | Cross et al. | |
| 2011/0190650 A1* | 8/2011 | McNair | A61B 5/0004 600/518 |
| 2011/0237922 A1* | 9/2011 | Parker, III | A61B 5/1112 600/382 |
| 2012/0088999 A1 | 4/2012 | Bishay et al. | |
| 2012/0245439 A1* | 9/2012 | Andre | A61B 5/0022 600/595 |
| 2013/0116533 A1 | 5/2013 | Lian et al. | |
| 2013/0158423 A1 | 6/2013 | Kapoor | |
| 2016/0029906 A1* | 2/2016 | Tompkins | A61B 5/6833 600/509 |
| 2018/0020931 A1* | 1/2018 | Shusterman | A61B 5/02116 600/483 |

OTHER PUBLICATIONS

Extended European Search Report for Application No. 19171646.3-1115 dated Jul. 18, 2019.

* cited by examiner

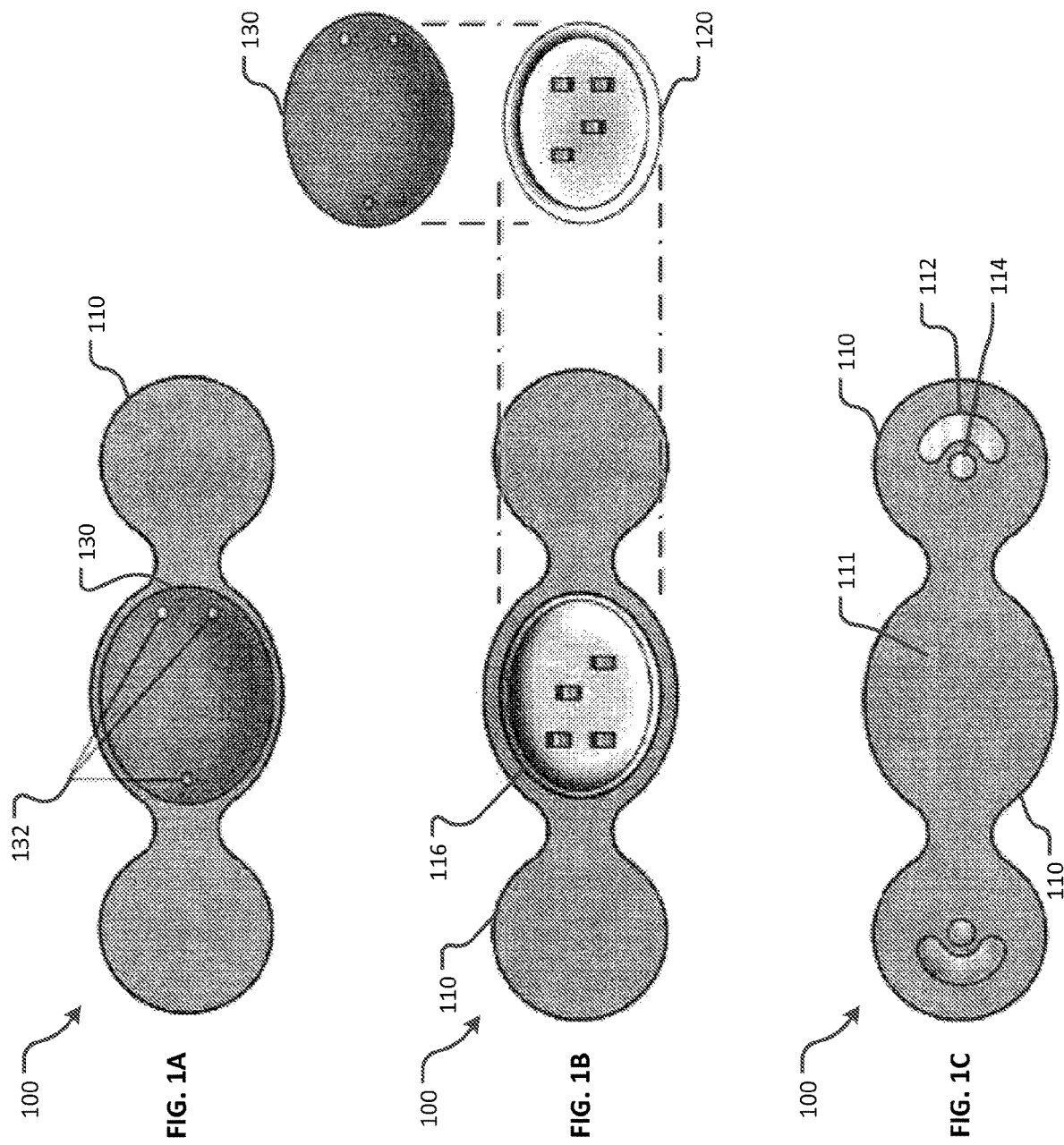

SENSOR TYPES AND SENSOR POSITIONING FOR A REMOTE PATIENT MONITORING SYSTEM

CROSS-REFERENCE TO RELATED APPLICATIONS

This application is a § 371 U.S. National Stage of International Application No. PCT/US2014/045030, filed Jul. 1, 2014, which claims the benefit of U.S. Patent Application No. 61/841,862, filed Jul. 1, 2013, the disclosures of which are all herein incorporated by reference in their entirety.

BACKGROUND

1. Technical Field

This document relates to devices and methods for monitoring health patient parameters using a wearable monitoring device. For example, this document relates to the use monitoring devices with multiple sensors, multiple types of sensors, algorithms for managing the multiple sensors to enhance monitor performance, and for detection of health events using health parameter data that is acquired by the monitoring system.

2. Background Information

For a variety of reasons, the importance of remote health monitoring systems, such as in-home monitoring systems, is increasing. Remote health parameter monitoring of ambulatory patients enables doctors to detect or diagnose health problems, such as heart arrhythmias, that may produce only transient symptoms and therefore may not be evident when the patients visit the doctors' offices. Remote health parameter monitoring is a significant tool available to healthcare providers for reducing hospital readmission rates and to track disease progression. The use of monitoring systems can permit a smooth transition from hospital to home care. Steadily increasing healthcare costs and outpatient populations have created a need to maximize time intervals between office visits.

The relentless pressure to reduce costs in the healthcare industry has required the more efficient use of a healthcare professional's services. As a result, many physicians now regularly prescribe home monitoring of such health parameters as blood pressure, heart rate, blood glucose level, and EKG (electrocardiogram) signals. In addition, health insurance providers are increasingly viewing remote health parameter monitoring as a means to reduce in-patient expenses and overall healthcare costs.

SUMMARY

This document provides devices and methods for monitoring health patient parameters using a wearable monitoring device. For example, this document provides monitoring devices with multiple sensors, multiple types of sensors, algorithms for managing the multiple sensors to enhance monitor performance, and for detection of health events using health parameter data that is acquired by the monitoring system.

In general, one aspect of this document features a method of using a computerized algorithm to identify and reduce artifact noise in a remote health parameter monitoring system. The method comprises: providing a sensor patch that is configured to be adhered to the skin of a patient, wherein the sensor patch includes a plurality of sensors for monitoring a health parameter; receiving by the monitoring system, a plurality of signals that originate from the plurality of sensors respectively; comparing, by the algorithm, the plurality of signals, wherein the comparing includes attempting to correlate an aspect of a first signal of the plurality of signals to a corresponding aspect of a second signal of the plurality of signals; determining, by the algorithm and based on the comparison of the plurality of signals, that certain sensors of the plurality of sensors are providing signals with less artifact noise than other sensors of the plurality of sensors; and based on the determination that certain sensors of the plurality of sensors are providing signals with less artifact noise than other sensors of the plurality of sensors, eliminating the use of the signals provided by the other sensors from being used by the monitoring system.

In various implementations, the plurality of sensors may include at least one EKG electrode and at least one accelerometer. The plurality of sensors may include at least one EKG electrode, at least one accelerometer, and at least one impedance sensor.

In another general aspect, this document features a method of using a computerized algorithm to enhance the accuracy of an EKG heart monitor system. The method comprises: adhering one or more sensor patches to a patient, wherein the one or more sensor patches include at least three electrodes that are configured to detect the EKG signals of the patient; determining, by the algorithm, multiple QRS complexes of the patient based on the respective signals provided by the three or more electrodes; comparing, by the algorithm, the multiple QRS complexes provided by the three or more electrodes to a characteristic QRS complex; and based on the comparison, eliminating, by the algorithm, at least one QRS complex of the multiple QRS complexes, wherein the at least one eliminated QRS complex is not used by the EKG heart monitor system for a determination of a final QRS complex, wherein the elimination is based on the at least one eliminated QRS having greater deviations from the characteristic QRS complex than other non-eliminated QRS complexes that are used by the EKG heart monitor system for the determination of a final QRS complex.

In various implementations, the one or more sensor patches may be a unitary sensor patch that includes the at least three electrodes. The unitary sensor patch may include six or more electrodes. The unitary sensor patch may include twelve or more electrodes.

In another general aspect, this document features a device for monitoring health parameters of a patient. The device comprises: a sensor patch that is configured to be in contact with a skin surface of the patient, wherein the sensor patch comprises a plurality of sensors for measuring physiologic or pathologic parameters of the patient, and wherein the sensor patch comprises two or more portions that are coupled using a flexible joint that is configured to allow the two or more portions to have independency of movement in relation to each other; a control unit, wherein the control unit is releasably receivable in a cradle of the sensor patch, and wherein the control unit is in electrical communication with the plurality of sensors when the control unit is in the cradle; and a cap, wherein the cap is configured to releasably couple with the sensor patch to detain the control unit in the cradle, and wherein the cap includes a user interface that is configured to provide indications of the functioning of the device.

In another general aspect, this document features a method of monitoring a patient using a health parameter monitoring system. The method comprises: providing a monitoring device; adhering a first of the at least three sensor patches over an anterior chest wall at a fourth intercostal space over the mid-sternum; adhering a second of the at least three sensor patches over an anterior chest wall at a fifth intercostal space over the mid-sternum; adhering a third of the at least three sensor patches over an anterior chest wall at a sixth intercostal space over the mid-sternum; and collecting, by the control unit, signals from sensors located in the first, second, and third sensor patches. The monitoring device comprises: at least three sensor patches that are configured to be adhered to a skin surface of the patient, wherein the sensor patch comprises a plurality of sensors for measuring physiologic or pathologic parameters of the patient; a control unit, wherein the control unit is releasably receivable in a cradle of the monitoring device, and wherein the control unit is in electrical communication with the plurality of sensors when the control unit is in the cradle; and a cap, wherein the cap is configured to releasably couple with other portions of the monitoring device to detain the control unit in the cradle, and wherein the cap includes a user interface that is configured to provide indications of the functioning of the device.

In various implementations, the sensors located in the first, second, and third sensor patches may be EKG electrodes.

Particular embodiments of the subject matter described in this document can be implemented to realize one or more of the following advantages. In some embodiments, an integrated health monitoring system based on acquisition of physiologic and pathologic parameters from sensors can facilitate ambulatory care to promote patient independence and permit a smooth transition from hospital to home care. In some embodiments, the algorithms provided herein can be used to increase the accuracy of the data collected by a health monitoring system by detecting and rejecting some signals as artifact noise, and by comparing various signals to cross-corroborate and optimize signals. In particular embodiments, the algorithms provided herein can enable enhanced detection of heart arrhythmia conditions. In some embodiments, the monitoring devices provided herein include sensor portions that can be remotely located from the central portion of the monitoring device. In some examples, the location of the sensor portions on the patient can be selected to provide low levels of signal noise from musculature movements. In result, the accuracy and effectiveness of health parameter monitoring systems can be improved, overall healthcare costs can be reduced, and patient health and longevity can be enhanced using the devices and methods provided herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIGS. 1A-1C are illustrations of a modular external patient monitoring device in accordance with some embodiments provided herein.

Like reference numbers represent corresponding parts throughout.

DETAILED DESCRIPTION

Figure 3:
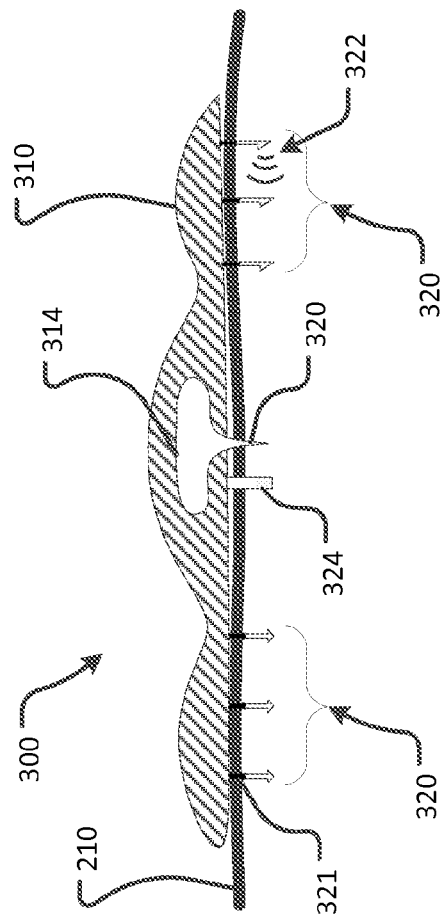
FIG. 3 is a side cross-sectional view another modular external patient monitoring device in accordance with some embodiments provided herein.

This document provides devices and methods for the remote monitoring of patient health parameters. For example, this document provides monitoring devices with multiple sensors, multiple types of sensors, algorithms for managing the multiple sensors to enhance monitor performance, and for detection of health events using health parameter data that is acquired by the monitoring system. In some embodiments, the remote health parameter monitoring system includes a wearable component and a separate computing device that can communicate with each other as well as with a remote monitoring service. In some embodiments, a controller unit in the wearable component performs the algorithms for artifact rejection and for detection of cardiac events. In other embodiments, the separate computing device performs the algorithms for artifact rejection and for detection of cardiac events. In some embodiments, both systems can perform such algorithms. While the algorithms provided herein may be described in the context of particular health parameter monitoring systems, it should be understood that the algorithms and techniques embodied in the algorithms can be applied to other monitoring systems or to the data of other monitoring systems.

A number of techniques for enhancing the accuracy and effectiveness of health parameter monitoring systems are provided herein. For example, particular monitoring system configurations and associated algorithms that can be used with the particular monitoring system configurations are provided herein. In one embodiment a monitor system includes a sensor patch having an array of sensors, such as ECG electrodes and other types of sensors. The control unit in the wearable monitor device, or another computing device of the monitoring system, can operate an array algorithm that compares and analyzes the data signals from the array of sensors to selectively determine which sensors of the array of sensors are providing the most accurate data (e.g., with the least artifact or with the best signal characteristics). In a further example, another sensor, such as an accelerometer, can identify a heartbeat movement, and the accelerometer signal can be compared with the ECG electrodes. This comparison can be performed in attempt to corroborate the signals from the ECG electrodes. Those signals of the ECG electrodes that are found to be the most synchronous with the accelerometer signal can be selected as the highest quality ECG signals, and those signals not synchronous with the accelerometer signal can be filtered.

Various configurations of wearable monitoring devices are also provided herein. Some of the monitoring devices provided herein have sensor portions that are flexibly positionable on the patient's skin in relation to other portions of the monitoring device. In some instances, this flexible positioning feature can be used effectively for reducing the biomuscular artifact signal noise that may be produced when the patient makes movements in the areas on which monitoring devices are positioned. Some embodiments of monitoring devices provided herein include remotely positionable sensor portions. That is, one or more sensor portions of the monitoring device can be positioned on the patient's skin at a location that is remote from another portion of the monitoring device. Such a feature allows for the optimization of the positioning of the sensor portions at particular locations on the patient to improve the signal-to-noise ratio of the sensors. Particular locations on the patient are identified herein that can be advantageously utilized by the health parameter monitoring systems provided. In addition, some embodiments of the monitoring systems provided herein are configured to provide patient fall detection.

The health parameter data collected from sensors on a patient can be communicated from a wearable monitor device to data collection and analysis systems in a variety of modes. In some implementations, the monitor device can wirelessly transmit data to a cellular telephone that is coupled via a short-range wireless link to a transceiver, and the transceiver can communicate over a network such as the internet to a remote monitoring server. In some implementations, a control module from the wearable monitor device can be decoupled from the monitor device and coupled to a base station, computing device, docking device coupled to a computing device, and the like. The health parameter data can then be downloaded from the control module to the base station, and the base station can communicate the data to a remote monitoring server over a network (including, for example, telephone landline or cellular phone networks). In some embodiments, a combination of such techniques and other techniques well known in the art can be used to communicate the health parameter data collected by the monitor device to a remote location for data monitoring and analysis.

The sensors used in the monitoring devices provided herein can include a variety of types and configurations. Some sensors are non-invasive. That is, some sensors make contact with the skin surface of the patient. Other sensors penetrate the dermal layers of the patient. Such penetrating sensors may also be referred to herein as "microneedles" or "microsensors." Microneedles can advantageously eliminate signal interference from the patient's skin in some circumstances. Therefore, microneedles may provide enhanced signal reception for parameters including but not limited to electrocardiography (ECG), electroencephalography (EEG), electromyography (EMG), and others. The monitoring devices provided herein may be used to collect other data types including but not limited to blood pressure, weight, hip waist ratio, oximetry, thoracic, bioimpedance, physical activity, temperature, drug levels, microfluidics (including serum and urine analytes and protein-based assays), respiration rate, heart sounds, voice recordings, heart rate (heart rate), posture, analyte values such as blood glucose, just to provide a few more examples. Movement or activity may be sensed with appropriate accelerometers or multi-axis gyroscopes, such as micro electro-mechanical system (MEMS) devices. Such collected data may in turn be synthesized using various algorithms to calculate other health status indicators such as QRS complex values, RR intervals, PVC values, arrhythmia, P wave, and others.

FIGS. 1A-1C provide an example wearable modular external monitoring device 100 shown in a top view (FIG. 1A), an exploded top view (FIG. 1B), and a bottom view (FIG. 1C). The modular external monitoring device 100 depicted includes a sensor patch 110, control unit 120, and a snap-on monitor 130. Sensor patch 110 includes a central cradle 116 that is a receptacle for releasably receiving control unit 120. With control unit 120 installed in cradle 116, snap-on cap 130 can be installed onto sensor patch 110 over control unit 120 to detain control unit 120 in sensor patch 110 as shown in FIG. 1A. Snap-on cap 130 can engage with complementary physical features on the sensor patch 110 so as to snap in place using a mechanical fit, for example. In some embodiments, snap-on cap 130 engages with sensor patch 110 to create a water-resistant seal therebetween.

When control unit 120 is installed in sensor patch 110, electrical connections are made such that control unit 120 is in electrical communication with the sensors that are visible on the bottom of sensor patch 110. Sensor patch 110 includes, in this example embodiment, an ECG electrode 112 and a bioimpedance sensor 114. However, a wide variety of types, configurations and numbers of sensors can be included in sensor patch 110 as described further herein, and as known in the art.

Some portions of modular external monitoring device 100 sensory and monitoring systems are located in sensor patch 110, and other portions are located in control unit 120 and snap-on cap 130. For example, in this embodiments sensor patch 110 includes the sensor devices, such as ECG electrode 112 and bioimpedance sensor 114. A power source such as a battery (not shown), and electrical contacts that mate with complementary contacts on control unit 120 can also be included in the sensor patch 110. Control unit 120 can include microelectronics including but not limited to a CPU, data storage memory, wireless transceiver, power management circuitry, sensor interface circuitry, alarm devices, and complementary contacts that mate with sensor patch 110 and snap-on cap 130. Snap-on cap 130, in addition to contacts that mate with control unit 120, can include user interface devices such as LEDs, a numeric display, a text display, an icon display, audio alarm devices, visual alarm devices, and a combination of such user interface devices.

Sensor patch 110 can be made from compliant polymeric materials and can have an adhesive on a bottom surface 111. In some embodiments, sensor patch 110 can comprise a material that is well-suited for the convenient placement on the patient's skin, consistent retention thereon, and non-irritating skin contact. For example, sensor patch 110 can comprise a soft elastomer such as a thermoplastic elastomer, silicone, or the like.

Snap-on cap 130 can include indicator LEDs 132 (or another type of user interface). LEDs 132 can signal to the patient various messages such as errors, the proper functioning of monitoring device 100, if the monitoring device 100 is transmitting data, and the like. Snap-on cap 130 can be a polymeric material. In some cases, snap-on cap 130 is a more rigid material than sensor patch 110. For example, snap-on cap 130 can be made from any suitable material such as polypropylene, polystyrene, acrylonitrile butadiene styrene (ABS), polycarbonate, PVC, silicone, or the like.

As best seen in FIG. 1B, control unit 120 that includes the memory, CPU, communications, etc. can be reversibly attached/detached to sensor patch 110. Because of this arrangement, a particular control unit 120 can be used with multiple properly configured sensor patches 110, and conversely, multiple properly configured control units 120 can be used with a particular sensor patch 110. In one example scenario of operating monitoring device 100, a patient can be given two control units 120 that are programmed and personalized identically. The control units 120 are rotated daily. That is, each day the patient removes a control unit 120 and installs the other control unit 120. The following day, the patient repeats the process—again swapping control units 120. In this manner, a particular control unit 120 gets used every other day. This usage of control units 120 can be independent of the patient's frequency of replacing sensor patches 110.

The control unit 120 that is removed from sensor patch 110 and is not in use on a particular day is installed onto a base station computer system. The base station can be located in the patient's home, at a treatment site, or a combination of such locations. The base station has network access (wired or wirelessly) and a standard AC power supply. In some cases, a cellular phone or other portable computing device can be used instead of the base station. The base station then downloads the health parameter data from control unit 120 and either stores the data to the data storage system of the base station or transmits the data to a monitoring service via the network. Further analysis of the data can be performed by the base station, monitoring service, and by health practitioners using the systems. Data can be presented graphically. Trends can be compiled and displayed. Various types of algorithms can be applied to provide artifact management, arrhythmia detection and other types of data analysis and diagnostic tools.

While control unit 120 typically downloads the health parameter data to a base station or equivalent device, in some cases control unit 120 while installed in the sensor patch 110 can send wireless transmissions to the base station or over cellular networks based on triggering events. Such triggering events can be determined for a particular patient and programmed into control units 120 for the patient. For example, a triggering event may be a particular variability in RR over a short time period, or an ECG QRS morphology, or the like.

Figure 2:
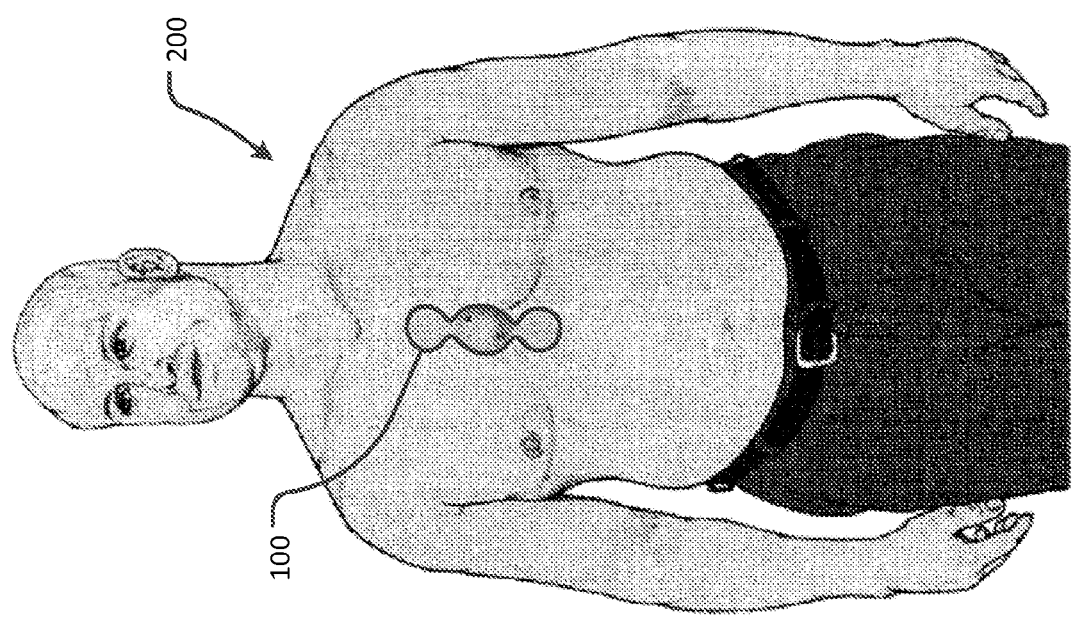
FIG. 2 is an illustration of a patient wearing the modular external patient monitoring device of FIGS. 1A-1C.

Referring to FIG. 2, a patient 200 is illustrated wearing modular external monitoring device 100. Monitoring device 100 is adhered to the skin of patient 200. In this example, monitoring device 100 is on the chest of patient 200 in a position over the sternum to measure heart and respiratory health parameters. This position is less prone to motion artifact than some other locations, because the skeletal and muscle motion above the sternum is generally minimal still, in other implementations monitoring device 100 is worn on other areas of patient 200. For example, monitoring device 100 may be worn on the head, abdomen, back, side, extremities, and other suitable locations on patient 200. The location on of monitoring device 100 on patient 200 will depend on the type of health parameter data to be collected.

Referring to FIG. 3, a cross-sectional side view of another example modular external monitoring device 300 is depicted on the skin 210 of a patient. Monitoring device 300 includes microneedles 320 that can be employed as sensors, injection devices, sampling devices, and for other like purposes. Microneedles 320 can be barbed or otherwise include structures which facilitate adherence to skin 210.

Microneedles 320 penetrate the skin 210 and the distal tips of the microneedles 320 reside subdermally. Therefore, microneedles 320, when used as sensors, have enhanced signal reception (e.g., for ECG, EEG, EMG, etc.). The enhanced reception can be due to the elimination of "shielding" by dermal layers to outside interference as well as because of closer proximity to organ to be monitored. In another implementation, microneedles 320 have access to interstitial fluid for sensing electrolytes, glucose, oxygen, pH, temperature, and so on. The portions of microneedles 320 near sensor patch 310 can be insulated portions 321 such that the only electrical recording would come from the exposed electrodes at the distal end of microneedles 320 that are positioned deeper into the tissue. In some cases, this arrangement can reduce signal artifact caused by patient motion or from intermittent contact between skin 210 and a surface electrode (e.g., electrodes 112 and 114 of FIG. 1C). Further, there are known electrical potentials that arise from the surface of skin 210 which can be a source of electrical noise. The avoidance of recording from the surface of skin 210 can decrease or eliminate this source of electrical noise.

In some cases, a set of two or more microneedles 320 can function as bipolar electrodes. That is, microneedles 320 can send and receive signals between microneedles 320 as depicted by signal symbol 322, or alternatively between the distal tip and mid-shaft of an individual microneedle 320.

Some embodiments of microneedles 320 can carry fiber optic elements and can transmit light for oximetry sensing. Light attenuation through tissue relates to oxygen tension, using techniques known in the field. The approach of embedding the transmittance and measurement of light within the dermal layers solves the problem of the difficulties with reflective oximetry whereby a patch is applied to a flat region of tissue (e.g. chest or back). In one embodiment, a first microneedle 320 has a side aperture to transmit light. A neighboring microneedle 320 has a complementary side aperture to receive the light transmitted from the first microneedle 320 via the tissue. Thus, the actual technique is transmissive from two neighboring microneedles 320 placed in the tissue. In another embodiment, light is transmitted from a microneedle 320 and the light transmitted through the tissue is received at a sensor on the bottom surface of sensor patch 310. This embodiment could rely on measurement of reflective light or transmissive light, depending on geometric arrangement of the microneedle 320 relative to the base of sensor patch 310.

In some embodiments, microneedles 320 can alternatively be used for drug delivery by injecting medication from a reservoir 314 located within or coupled to sensor patch 310. For example, a drug such as a steroid, lidocain, and others can be beneficially administered to the patient to prevent discomfort and inflammation which could otherwise result from the chronic use of sensor patch 310 and microneedles 320. In another example, an agent can be delivered from reservoir 314 through microneedles 320 to treat a patient's particular detected disorder. Drugs such as quinidine, beta-blocker, amiodarone, insulin, and so on can be used in such applications.

Microneedles 320 may also include accelerometers at distal tips to help with the control of signal noise from the sensors. For example, movement sensed at microneedle 320 tip by an accelerometer can indicate motion and typical signal noise associated with such motion can be anticipated and managed. In some cases, electrical circuitry or software can be used for cancellation, correction, and filtering of the resulting signal to thereby reduce motion artifact. Previous attempts to record signal noise using accelerometers at locations removed from the recording electrode—even by a small amount—have been ineffective due to the lack of correlation between the forces at the accelerometer and at the electrode. An accelerometer in microneedle 320, or at the base of the microneedle 320, can resolve that problem.

In some embodiments, monitor device 300 can also include one or more piezoelectric sensors 324. Piezoelectric sensors 324 can be used to measure bioimpedance which can in turn provide a useful signal for artifact elimination, arrhythmia detection, determination of respiration rate, and other purposes.

Figure 4A:
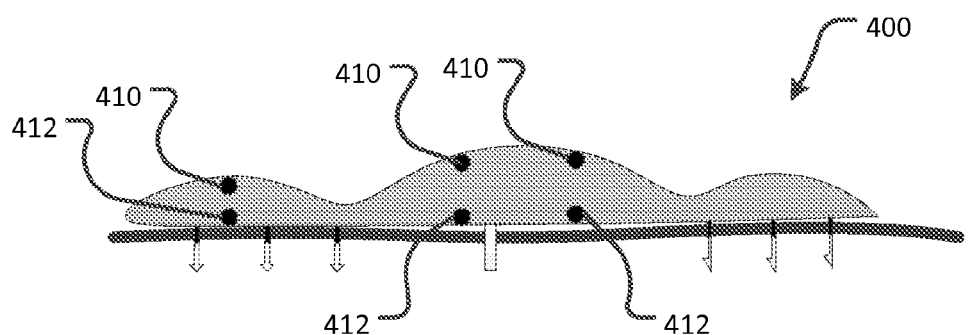
FIGS. 4A and 4B are illustrations of additional modular external patient monitoring devices in side cross-sectional views in accordance with some embodiments provided herein.

In reference to FIG. 4A, a modular external monitoring device 400 is illustrated including one or more upper accelerometers 410 and one or more lower accelerometers 412. In some embodiments, multi-axis gyroscopes can be used in addition to or as a substitute for accelerometers 410 and 412.

Including accelerometers 410 and 412 in monitoring device 400 can provide many advantages. In some embodiments, monitoring device 400 only captures or analyzes data when motion levels as determined by accelerometers 410 and 412 are below certain thresholds levels (so as to avoid motion artifact). Accelerometers 410 and 412 can be oriented in multiple arrangements to facilitate several functions (e.g. physiologic monitoring and device function). For example accelerometers 410 and 412 can be incorporated into the monitoring device 400 platform as independent sensors, or into the electrodes themselves (as described herein). Integration of motion data at the electrode interface may be beneficial when correlated with motion at a distance—away from the electrodes—this would allow for noise subtraction due to motion of monitoring device 400.

Further uses for accelerometers 410 and 412 can include physiologic monitoring. For example, physical activity or inactivity—including "learned" activities, can be measured, and correlations of these learned activities with expected changes in other monitored/sensed data inputs can be used to enhance the value of the data collected my monitoring device 400. Signals from accelerometers 410 and 412 can be used to indicate patient falls, long-term inactivity, and levels of activity. Heart sounds and motion permitting event timing and ECG can be detected by accelerometers 410 and 412 in some embodiments. Respiration can be determined based on motion of monitor device 400, bioimpedance changes, or both. Accelerometers 410 and 412 can also be used to determine erect or supine posture. All of these measurements can be combined and cross-checked to determine the presence of artifact and/or increase the sensitivity and specificity of event recording.

Signal noise (artifact) can be very difficult to distinguish from potentially dangerous and rapid heart rhythms. Artifact may be caused by a number of conditions, with the two primary ones being (1) mechanical motion with subsequent myopotentials and (2) poor electrode contact. With poor electrode contact, bioimpedance may be useful particularly when supplemented with data from accelerometers 410 and 412. With physical/mechanical motion, accelerometers 410 and 412 could be useful in determining that artifact is present secondary to motion data from accelerometers 410 and 412. The physical motion that results in ECG artifact can have a characteristic "signature" unique to a specific activity such as walking and other routine activities, tremor, or local skeletal muscle contraction. Thus, rather than performing artifact rejection, the monitoring device 400 would be programmed to detect artifact and classify it as such using the "noise signature" that results from characteristic ECG signals. These unique activity signatures can be taught to the control unit during registration and thereby enhance signal quality and event detection, by artifact detection and rejection.

The location of the accelerometers 410 and 412 can be advantageously selected to enable artifact signal noise detection. Integration of accelerometers onto electrodes as described herein is a good approach. For example, in some embodiments a first accelerometer is embedded in a microneedle or other type of sensor, and a second accelerometer is located in the sensor patch (such as on a circuit board of the control unit). Analysis of the relative motion of these two accelerometers would be useful in developing these characteristic "signatures" of particular types of motion. For example, an individual's stride during walking would likely result in similar motion detected by accelerometers in contact with the skin and by accelerometers on the circuit board, whereas as the type of motion associated with myopotentials (e.g., pectoralis motion) or vibratory motion from riding in a car on a bumpy road may result in different signals from the two accelerometers. If these "noise" motion signals occur in the setting of "high heart rates" it can indicate likely artifact. For example, radial motion such as may be expected with a swinging of the arms or movement of the pectoralis would result in a greater translational motion of the upper accelerometer 410 than a lower accelerometer 412. This difference can be taken advantage of to define a characteristic signature to each type of motion and thus identify specific activities. For example, if a person is traveling in a car and not otherwise moving, then accelerometer 410 would equal accelerometer 412, as both accelerometers 410 and 412 are being equally translated by the car's movement. In contrast, if a person is actively rowing a boat, then accelerometer 410 would be far greater than accelerometer 412, thus providing for the detection of this type of activity.

Accelerometer 410 and 412 data in combination with other data such as ECG and impedance data can also be used to indicate poor contact of monitoring device 400 with the patient. In turn, monitoring device 400 can alert the patient or other personnel, reject certain data signals, and so on. The user of multiple accelerometers 410 and 412 can be used to enhance this function. For example, if signals from accelerometers 410 shows motion analogous to accelerometers 412 then skin contact may be lost. Accelerometer 410 motion should be less than that of accelerometer 412 when monitor device 400 is correctly placed and in correct skin contact.

Figure 4B:
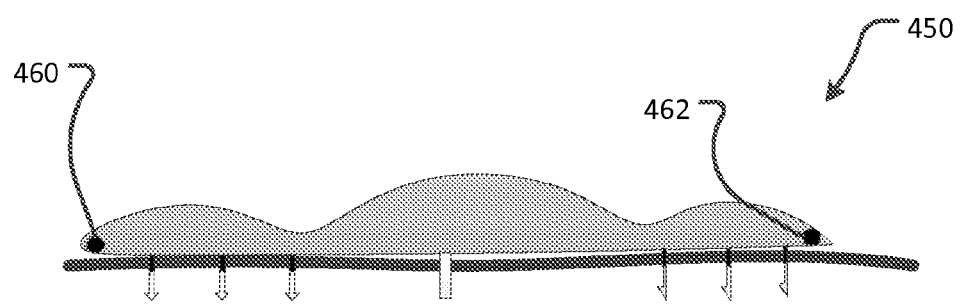

In reference to FIG. 4B, a modular external monitoring device 450 is illustrated including one or more first end accelerometers 460 and one or more second end accelerometers 462. In some embodiments, multi-axis gyroscopes can be used in addition to or as a substitute for accelerometers 460 and 462.

Similar to the functionality of accelerometers 410 and 412 as described herein, the relative motion between accelerometers 460 and 462 can indicate monitor device 450 that is being twisted or otherwise improperly configured. Such a motion could indicate a poor contact with the patient's skin such as a detachment of a "wing" or end portion of monitoring device 450.

In some embodiments, a combination of vertically differentiated accelerometers (410 and 412) and horizontally differentiated accelerometers (460 and 462) can be used on a single monitoring device. In addition, other sensors such as a temperature sensor embedded near an electrode can be included to enhance detection of improper placement or detachment of monitoring device 450 from the patient's skin. For example, a temperature sensor may indicate a sudden change in temperature or sudden drop in temperature that indicates poor electrode contact with the patient's skin.

Figure 7:
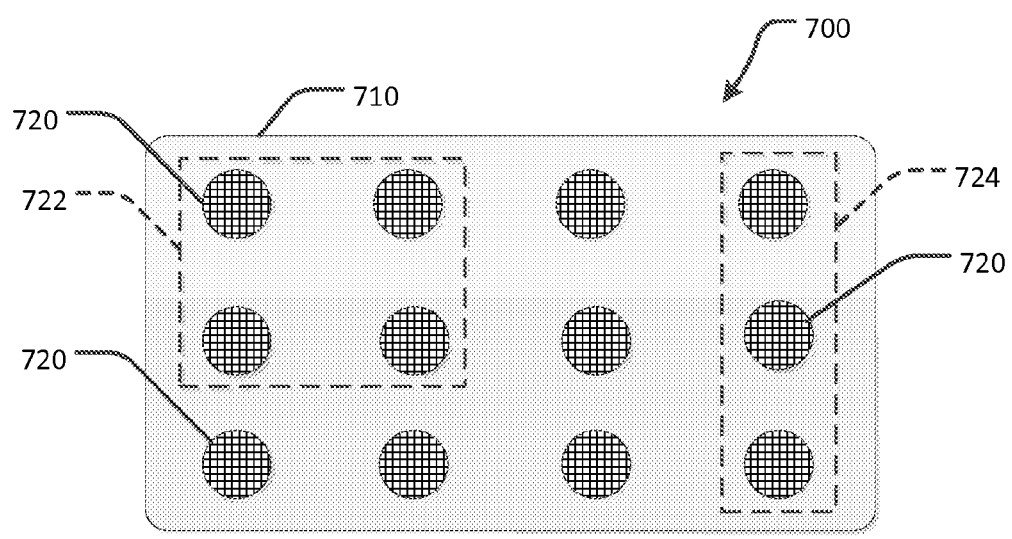
FIG. 7 is an example sensor patch that can be used with an algorithm to detect and manage artifact.

In reference to FIG. 7, an example embodiment of a wearable sensor patch 700 that can be used in conjunction with an electrode array algorithm for artifact management is provided. While the algorithm is described here in the context of the sensor patch 700, it should be understood that the algorithm can be used for other types of sensors and combinations of different types of sensors, including sensors that are not all on the same patch. In some embodiments, different types of sensors that provide like results can be compared, and the best selected by the algorithm as described herein.

The sensor patch 700 includes a flexible base 710 with an adhesive coating and an array of sensors 720 (also referred to herein as "multi-array sensors"). This type of sensor patch 700 can be used with the electrode array algorithm that can analyze the data signals from multi-array sensors 720 to selectively determine which sensors of multi-array sensors 720 are providing the most accurate data, and with the least artifact or with the best signal characteristics. This embodiment also includes a control unit that can be either located on sensor patch 700, or remotely located from sensor patch 700.

The electrode array algorithm can sample sensor signals and operate either continuously or periodically on a real-time basis to select data from two or more electrodes or groups of electrodes that are providing the best data from among multi-array sensors 720. This algorithm provides identification of poor quality data from one or more electrodes, and permits rejection of the signal input from such an electrode in the final ECG analysis. This algorithm also provides identification of the best combination of signals based on certain electrocardiographic parameters (e.g., based on comparisons to characteristic QRS complexes, and/or characteristic P wave morphology), and allows these best signals or a combination thereof to be used for final ECG analysis. For example, a sub-group of electrodes 722 may be identified by the electrode array algorithm as providing the best quality data, and therefore the data from electrode sub-group 722 is used for the final ECG analysis. In another example, a sub-group of electrodes 724 may be identified by the electrode array algorithm to be providing the best quality data, and therefore the data from electrode sub-group 724 is used for the final ECG analysis. In some embodiments, the signals from multi-array sensors 720 are compared to a reference electrode and its attributes to assist in the identification of signals from multi-array sensors 720 that are providing the best quality data.

In a related embodiment for the selection of optimal signal generating electrodes (or other sensors) to improve ECG signal identification, three or more skin surface electrodes can be positioned on a patient's body in locations that are selected to improve the electrode's signal-to-noise ratio. This technique can be used in combination with an algorithm permitting real-time data selection from two or more of these electrodes, and incorporation of additional physiologic sensors to cross-correlate with the signals from the electrodes.

Such an embodiment can incorporate an advantageous orientation and spacing of three or more skin surface electrode patches to detect physiologic signals (e.g., electrocardiograms) to improve signal-to-noise ratio. Optimal electrode placement in patients under different conditions including resting supine, resting standing, and walking have been discovered and are provided herein. That is, optimal lead positions and spacings, which provide adequate ECG signal with reduced biomuscular artifact, have been identified. The locations are over the anterior chest wall between the fourth, fifth, and sixth intercostal spaces over the midsternum. These positions are less prone than other positions to pectoralis contraction, thereby resulting in less motion of the surface electrodes and less detection of biomuscular signal noise.

An example algorithm for "multiple electrode real-time selection" permitting real-time data selection from three or more electrodes is provided here. This algorithm permits identification of poor quality data from one or more electrodes (using, e.g., the algorithms for artifact management provided herein) and permits the rejection of the signal input from such an electrode in the final ECG analysis. This algorithm also permits identification of the best combination of signals based on certain electrocardiographic parameters (e.g., characteristic QRS complexes and/or characteristic P wave morphology) and allows these best signals, or a combination thereof, to be used for final ECG analysis. Additional physiologic sensor inputs can also be used in the algorithm. For example, one or more accelerometers can be used to detect motion artifact, including gross locomotion and fine muscle motion (including tremor and local skeletal muscle contraction). In another example, an audio sensor input can be used in the algorithm to detect heart sounds to permit event timing and ECG signal correlation. In still another example, one or more accelerometers can be used to detect respiration, and the determination of either erect or supine posture can be made therefrom, which can be input to the algorithm. One or more sensors (e.g., accelerometers, gyroscopes, microphones, impedance sensors, and the like) can acquire the above physiologic information (and other types of information), segment the data based on differential filtering, and then present this segmented information for analysis by the multiple electrode real-time selection algorithm.

While the embodiment shown in FIG. 7 is depicted as a single sensor patch, in alternative embodiments the electrode array algorithm is used with multiple electrodes or other types of sensors that are not all positioned on a single sensor patch, or are positioned on various types of sensor patches other than the configuration shown in FIG. 7. Various types of other sensor patch embodiments are illustrated herein, and still others are envisioned and described though not specifically illustrated.

Figure 6:
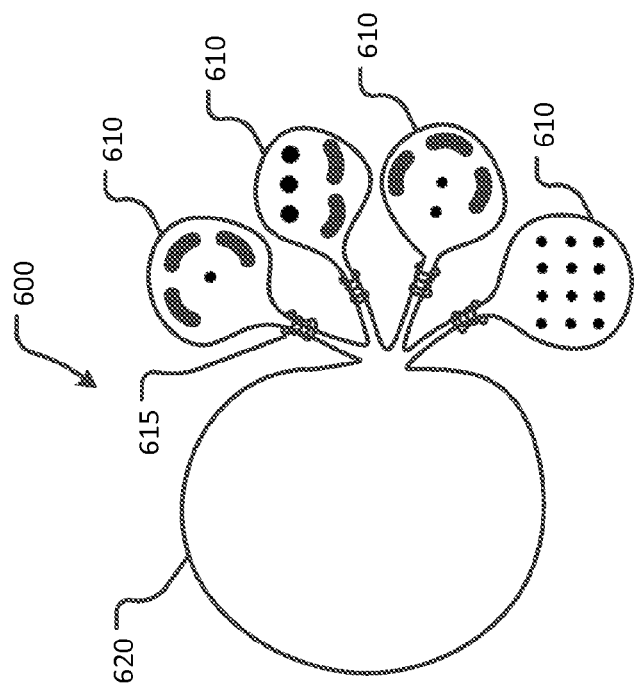
FIG. 6 is an illustration of another modular external patient monitoring device in accordance with some embodiments provided herein.
Figure 5B:
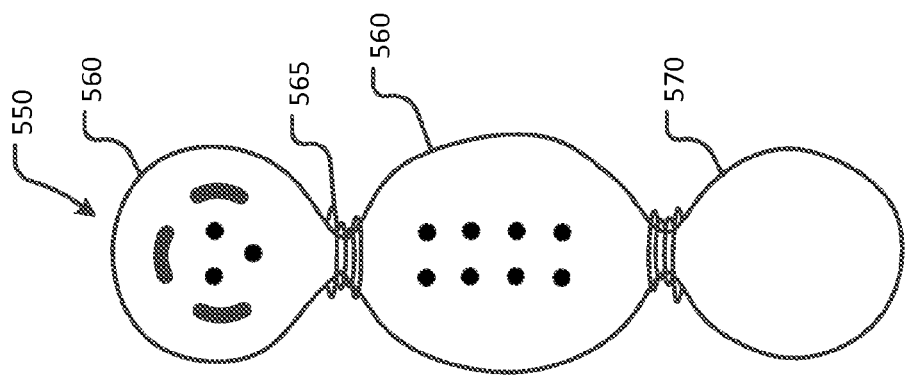
FIGS. 5A and 5B are illustrations of additional modular external patient monitoring devices in accordance with some embodiments provided herein.
Figure 5A:
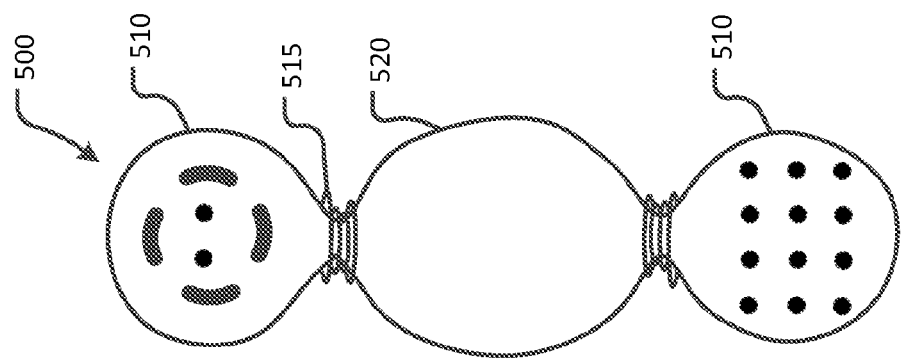

Referring to FIGS. 5A, 5B, and 6, additional example sensor patch embodiments are provided. That is, monitoring devices 500, 550, and 600 are depicted, respectively, in FIGS. 5A, 5B, and 6. As illustrated, a wide variety of monitoring device and sensor patch configurations are envisioned. The configurations may be tailored for use on a certain part of a patient's anatomy or on a certain body size. In general, each monitoring device 500, 550, and 600 includes sensor portions 510, 560, and 610 respectively. The sensor portions 510 and 610 may also be referred to as wings due to their configuration as extensions from a main portion 520 and 620. Further, each monitoring device 500, 550, and 600 includes a location for a control unit 520, 570, and 620 respectively. As shown by FIG. 5B, in some embodiments the control unit 570 is located on a wing of the monitoring device 550, and sensors are located in the central portion. Any, and all, combinations of such features are envisioned in the scope of this disclosure. Monitoring devices 500, 550, and 600 can function as described herein in relation to other embodiments of monitoring devices.

Monitoring devices 500, 550, and 600 also include flexible connection joints 515, 565, and 615 respectively. Flexible connection joints 515, 565, and 615 allow the wings to be advantageously movable in relation to the main portions of the monitoring devices 500, 550, and 600. This feature can provide a variety of benefits. For example, in some situations this feature can allow the wings to be initially adhered to the skin of a patient in a desirable location, with reduced physical constraints from the orientation of the main portion of the monitoring devices 500, 550, and 600. In addition, flexible connection joints 515, 565, and 615 can reduce the signal noise (artifact) generated by physical movements of the patient. That is, flexible connection joints 515, 565, and 615 enable greater conformability and integrity of adherence of monitoring devices 500, 550, and 600 to the patient's skin when the patient makes movements in the areas on which monitoring devices 500, 550, and 600 are adhered.

In an alternate embodiment, the sensor portions (e.g., electrode arrays and other types of sensors) can be connected to the main portion of the monitor device (e.g., the control unit) using an extendable and retractable wiring configuration. In some embodiments, a spring-actuated spool located on the main portion of the monitoring device can provide this feature. In other embodiments, any excess wire can be manually wound onto a spool located on the main portion, or simply bundled up and retained on the main portion or the skin of the patient. In still other embodiments, the wiring can be configured of detachable leads, and a variety of lengths of detachable leads can be available to be used to suit the particular application. This monitoring device configuration thereby allows for locating the sensor portions at various positions around the patient's body that may be remote from the position of the main portion of the monitor device on the patient's body.

In these embodiments with remotely located sensor portions, as with other particular embodiments provided herein, the signals from the electrodes and other types of sensors that are used for monitoring can be strategically selected by the control unit based on various factors and algorithms (e.g., signal quality, parameter to be measured, patient orientation, collaboration by other sensor signals, etc.). As such, the various electrodes and other sensors can be activated and deactivated in real-time by the control unit operating the algorithms. In some embodiments, multiple electrodes and/or sensors can be activated and can communicate within a wing or between wings to establish monitoring vectors, or to verify recording from one electrode/sensor with a reading from another. The control unit can contain algorithms to select the best electrodes or sensors to activate, and the algorithm can perform a continuous loop of the logic to thereby maintain optimal signals. Impedance changes between separate electrodes (on different wings or on the same wing) can be used to detect loss of contact of the monitoring device from the patient's skin. When a loss of contact is so detected, a corresponding alert can be sent by the monitoring device to the patient and monitoring service.

In some embodiments, the application of a monitoring device to the skin of a patient can be automatically detected by the monitoring device. In particular embodiments, such an automated detection can be performed by impedance monitoring, or physiologic variation in impedance, or ECG recognition, to provide some examples. When the monitoring device detects its application to the patient's skin, the monitoring device can automatically turn on so that the patient doesn't have to manually activate the monitoring device.

Some embodiments of the monitoring systems provided herein are configured to provide patient fall detection. Fall detection can be performed in various manners. In one example, a change in body position can be correlated with a pressure sensor, auditory event, heart rate change, or respiratory change to detect a fall. Such a system can use an accelerometer or gyroscope to detect body position. ECG electrodes, blood pressure monitoring devices, auditory sensors, and impedance sensors, and the like may provide the corroborating signal information by which an algorithm can make a conclusion that a fall has occurred.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products. Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A device for monitoring health parameters, the device comprising:
   a sensor patch including a cradle and configured to be in contact with a skin surface of a patient,
   wherein the sensor patch comprises a plurality of sensors for measuring physiologic parameters of the patient,
   wherein the sensor patch comprises a first wing, a first flexible joint, a second wing, a second flexible joint, and a central portion positioned between the first wing and the second wing,
   wherein the first flexible joint is positioned between the first wing and the central portion,
   wherein the second flexible joint is positioned between the second wing and the central portion,
   wherein the cradle is positioned on the central portion, wherein the first wing and the second wing are the only two wings extending from the central portion of the sensor patch, wherein at least one of the plurality of sensors is positioned on the first wing and another one of the plurality of sensors is positioned on the second wing;

a control unit, wherein the control unit is releasably receivable in the cradle of the sensor patch, wherein the control unit is in electrical communication with the plurality of sensors when the control unit is in the cradle; and a cap, wherein the cap is configured to releasably couple with the sensor patch to detain the control unit in the cradle, wherein the cap includes a user interface that is configured to provide indications of the functioning of the device.

2. The device of claim 1, wherein the control unit is programmed to send wireless transmissions of data in response to a triggering event.

3. The device of claim 2, wherein the triggering event comprises a variability in RR intervals over a period of time.

4. The device of claim 2, wherein the triggering event comprises a QRS morphology.

5. The device of claim 1, wherein the user interface comprises a visual indicator.

6. The device of claim 5, wherein the visual indicator comprises one or more light emitting diodes (LEDs).

7. The device of claim 1, wherein the cap is a snap-on cap configured for engagement with complementary features of the sensor patch.

8. The device of claim 7, wherein the snap-on cap is configured to engage with the sensor patch to create a water-resistant seal therebetween.

9. The device of claim 1, wherein the sensor patch comprises a thermoplastic elastomer.

10. The device of claim 9, wherein the cap comprises polypropylene.

11. The device of claim 1, wherein the first flexible joint is narrower than the first wing and the central portion.

12. The device of claim 11, wherein the second flexible joint is narrower than the second wing and the central portion.

13. The device of claim 1, wherein the plurality of sensors comprise electrodes.

14. The device of claim 1, wherein the user interface comprises an audio alarm.

15. The device of claim 1, wherein the sensor patch comprises a unitary sensor patch comprising three or more electrodes.

16. The device of claim 1, wherein the plurality of sensors includes at least one electrode and at least one accelerometer.

17. The device of claim 1, wherein the plurality of sensors includes an electrode, an accelerometer, and an impedance sensor.

18. The device of claim 1, wherein the sensor patch comprises a first material that is less rigid than a second material of the cap.

19. The device of claim 1, wherein the plurality of sensors comprises microneedles.

* * * * *